United States Patent [19]

Manero et al.

[11] Patent Number: 5,445,762

[45] Date of Patent: Aug. 29, 1995

[54] STABILIZED COMPLEX LIGANDS AND THEIR USE IN LIQUID CRYSTAL DISPLAYS

[75] Inventors: Javier Manero; Norbert Rösch, both of Frankfurt am Main, Germany

[73] Assignee: Hoechst Aktiengesellschaft, Frankfurt, Germany

[21] Appl. No.: 185,943

[22] PCT Filed: Aug. 19, 1992

[86] PCT No.: PCT/EP92/01895

§ 371 Date: Jan. 18, 1994

§ 102(e) Date: Jan. 18, 1994

[87] PCT Pub. No.: WO93/04142

PCT Pub. Date: Mar. 4, 1993

[30] Foreign Application Priority Data

Aug. 21, 1991 [DE] Germany .................. 41 27 658.2

[51] Int. Cl.⁶ .............. C09K 19/52; C09K 19/56; C07D 273/00
[52] U.S. Cl. .............. 252/299.01; 252/299.4; 252/299.6; 252/299.61; 544/65; 544/66
[58] Field of Search ............. 252/299.01, 299.5, 299.4, 252/299.6, 299.61; 544/65, 66

[56] References Cited

U.S. PATENT DOCUMENTS

| 3,674,811 | 7/1972 | Kern | 540/467 |
| 4,001,212 | 1/1977 | Richman | 540/474 |
| 4,267,256 | 5/1981 | Bloom et al. | 430/251 |
| 5,178,792 | 1/1993 | Harada et al. | 252/299.6 |
| 5,206,751 | 4/1993 | Escher et al. | 252/299.01 |

FOREIGN PATENT DOCUMENTS

| 0429662 | 6/1991 | European Pat. Off. |
| 541081 | 5/1993 | European Pat. Off. |
| 7433171 | 5/1975 | France. |
| 1953249 | 5/1970 | Germany. |
| WO91/08272 | 6/1991 | WIPO. |

OTHER PUBLICATIONS

Japanese Abstract No. 54 091 253.

*Primary Examiner*—Shean Wu
*Attorney, Agent, or Firm*—Curtis, Morris & Safford

[57] ABSTRACT

Decomposition-sensitive complex ligands can be stabilized by derivatizing them with the aid of bulky secondary or tertiary carboxylic acids or sulfonic acids. These stabilized derivatives can be added to alignment layers and liquid-crystal mixtures and increase the contrast and brightness in the FLC display.

10 Claims, 1 Drawing Sheet

FIG.1

STABILIZED COMPLEX LIGANDS AND THEIR USE IN LIQUID CRYSTAL DISPLAYS

BACKGROUND OF THE INVENTION

WO 91/08272 describes the use of complex ligands in ferroelectric liquid-crystal (FLC) mixtures or in alignment layers of liquid-crystal displays. These substances can be used to modify the alignment or switching behavior of the FLC mixtures to increase the contrast and brightness in the displays and to suppress the formation of ghost images.

However, it has been found in the course of time that complex ligands, in particular those containing nitrogen, decompose on exposure to light (UV light) and heat. The decomposition products are distinguished by a yellow color. If the nitrogen-containing complex ligands are dissolved in liquid crystals, the low stability of the complex ligands finally results in a yellow coloration of the liquid-crystal mixture. If the decomposition of the complex ligand is well advanced, the positive effect of the ligands can in the end even be lost.

SUMMARY OF THE INVENTION

Surprisingly, it has now been found that these substances can be stabilized by derivatizing them by means of bulky secondary or tertiary carboxylic acids or sulfonic acids. Compounds derivatized in this way have equally good effectiveness, for example for suppressing ghost images, as the underivatized compound and have the advantage that decomposition, and thus a yellow coloration of the liquid-crystal mixture, no longer occurs.

The invention thus relates to: 1. A compound of the formula I $$[(CH_2)_{\overline{a}}Z^1(CH_2)_b]_p[(CH_2)_{\overline{c}}Z^2-(CH_2)_d]_q[(CH_2)_{\overline{e}}Z^3-(CH_2)_f]_r \quad I$$
$$Y-N \qquad\qquad\qquad\qquad\qquad\qquad\qquad\qquad X$$
$$[(CH_2)_{\overline{g}}Z^4(CH_2)_h]_s[(CH_2)_{\overline{i}}Z^5(CH_2)_j]_t[(CH_2)_{\overline{k}}Z^6-(CH_2)_l]_u$$

in which
$Z^1$, $Z^2$, $Z^3$, $Z^4$, $Z^5$ and $Z^6$ are identical or different and are the —O—, —S—, groups,
or are a single bond, but where at least 3 of the Z groups must be present in the formula I,
and where $R^1$ and $R^2$ are identical or different and are $C_1$-$C_{18}$ alkyl or phenyl, which may be substituted by 1 to 3 $C_1$-$C_4$-alkyl or -alkoxy groups, or $R^1$ and $R^2$ together are —(CH$_2$)$_5$— or —(CH$_2$)$_6$—, and $R^3$ is hydrogen or $C_1$-$C_4$-alkyl,
Y is the B—(CH$_2$)$_m$—A— group, in which B is the group,
where $R^4$, $R^5$, $R^6$, $R^7$ and $R^8$ are identical or different and are an alkyl radical having 1 to 5 carbon atoms, or $R^4$ and $R^5$, $R^5$ and $R^6$, $R^6$ and $R^7$ and $R^7$ and $R^8$ in each case together form a ring, so that B is a naphthalene, phenanthrene or indene radical, and $R^9$, $R^{10}$ and $R^{11}$ are identical or different and are branched or unbranched alkyl having 1 to 6 carbon atoms, or together with the carrying carbon atom form a cyclic or polycyclic system having 2 to 12 rings, preferably 2 to 6 rings,
m is the number 0 or 1,
X is N—Y, —O— or $Z^1$ to $Z^6$,
a, b, c, d, e, f, g, h, i, j, k and l are a number from 0 to 3, where the sum of a+b+c+d+e+f+g+h+i+j+k+l preferably corresponds to from 8 to 16 carbon atoms, with the proviso that if a, f, g and/or l are the number zero, only the groups are bonded directly to N or X, and that $Z^1$, $Z^2$ and $Z^3$, and $Z^4$, $Z^5$ and $Z^6$ are not directly adjacent, and
p, q, r, s, t and u are the number 0 or 1, where the sum of p, q, r, s, t and u is preferably from 2 to 6;
a, b, c, d, e, f, g, h, i, j, k, l and p, q, r, s, t and u must be selected so that ring sizes of from 6 to 36, preferably from 12 to 24, arise.

DESCRIPTION OF THE PREFERRED EMBODIMENTS

Preference is given to compounds of the formula I in which Y is the following groups:

adamantylcarbonyl pivaloyl

-continued mesitylenecarbonyl

2,6 dimethylbenzoyl mesitylenesulfonyl cubanecarbonyl

[2.2.2]bicyclooctane-1-carbonyl adamantylacetyl adamantylthiouryl

-continued noradamantylcarbonyl

1-norbornanecarbonyl pagodanecarbonyl 3.3-dimethylbutyroyl 2.2-dimethylbutyroyl

Further particular preference is given to compounds of the formula I in which Y is the following groups:
adamantylcarbonyl
pivaloyl
adamantylacetyl
2,2-dimethylbutyroyl
3,3-dimethylbutyroyl
1-noradamantylcarbonyl.

The compounds of formula I can be prepared by the methods cited below:

1) Houben-Weyl, Methoden der Organischen Chemie [Methods of Organic Chemistry], 4th Edn., Vol. VIII, Oxygen Compounds III, pp. 653 to 671
2) Houben-Weyl, Methoden der Organischen Chemie [Methods of Organic Chemistry], 4th Edn., Vol. E4, Carbonic acid derivatives pp. 484 to 505
3) Houben-Weyl, Methoden der Organischen Chemie [Methods of Organic Chemistry], 4th Edn., Vol. El, Phosphorus compounds I, pp. 271 to 313
4) Houben-Weyl, Methoden der Organischen Chemie [Methods of Organic Chemistry], 4th Edn., Vol. El, Phosphorus compounds I, pp. 313 to 488
5) Houben-Weyl, Methoden der Organischen Chemie [Methods of Organic Chemistry], 4th Edn., Vol. E2, Phosphorus compounds II, pp. 394 to 398
6) Houben-Weyl, Methoden der Organischen Chemie [Methods of Organic Chemistry ], 4 th Edn., Vol. E2, Phosphorus compounds II, pp. 487 to 831

7) Houben-Weyl, Methoden der Organischen Chemie [Methods of Organic Chemistry], 4th Edn., Vol. E11, Organic Sulfur compounds I, pp. 655 to 662

8) Houben-Weyl, Methoden der Organischen Chemie [Methods of Organic Chemistry], 4th Edn., Vol. E11, Organic Sulfur compounds II, pp. 1098 to 1103.

The compounds of the formula I can be added to ferroelectric liquid-crystal mixtures and introduced into or onto alignment layers. The bonding to the alignment layer can take place via chemical coupling, i.e. covalent bonds, or by physisorption, i.e. by intermolecular attractive forces, to the alignment layer molecules. In the case of physisorption, the strength of the coupling to the alignment layer molecules can be increased by using highly polar compounds of the formula I.

The compounds of formula I are introduced into the liquid-crystal mixture or introduced into or applied to the alignment layer in concentrations of from 0.01 to 20% by weight, preferably from 0.1 to 5% by weight.

The examples below serve to further illustrate the invention.

EXAMPLES

Example 1

Synthesis of carboxylic acid halides from carboxylic acids 15 ml of a carboxylic acid are dissolved in from 30 to 100 ml of benzene, and 12 ml of oxalyl chloride and 2 drops of pyridine are added. After 18 hours, the solvent is stripped off 2×12 ml of benzene are added to the sample, the solvent is again stripped off, and the product is dried by means of an oil pump.

Example 2

4,10-Bis(tert.-butylcarbonyl)-1,7-dioxa-4,10-diazacyclododecane 3.81 mmol of 1,7-dioxa-4,10-diazacyclododecane are dissolved in 50 ml of $CH_2Cl_2$. 1.2 ml of triethylamine are added, and 0.1 g of DMAP (=4-dimethylaminopyridine) is added as catalyst. 7.64 mmol of pivalyl chloride are subsequently added, and the mixture is stirred at room temperature for 18 hours.

The reaction solution is washed twice with 1N HCl and subsequently twice with saturated $NaHCO_3$ solution and dried over $MgSO_4$, and the solvent is stripped off. The crude product is purified by column chromatography on silica gel using $CH_2Cl_2$/methanol=20/1.

Example 3

4,10-Bis(1-adamantylcarbonyl)-1,7-dioxa-4,10-diazacyclododecane

-continued

Analogously to Example 2 from 1,7-dioxa-4,10-diazacyclododecane and 1-adamantylcarbonyl chloride.

Example 4

4,10-Bis((1-adamantanyl) acetyl)-1,7-dioxa-4,10-diazacyclododecane

Analogously to Example 2 from 1,7-dioxa-4,10-diazacyclododecane and (1-adamantyl) acetyl chloride.

Example 5

7,13-Bis(tert.-butylcarbonyl)-1,4,10-trioxa-7,13-diazacyclopentadecane

Analogously to Example 2 from 1,4,10-trioxa-7,13-diazacyclopentadecane and pivalyl chloride.

Example 6

7,13-Bis(1-adamantylcarbonyl)-1,4,10-trioxa-7,13-diazacyclopentadecane

Analogously to Example 2 from 1,4,10-trioxa-7,13-diazacyclopentadecane and 1-adamantylcarbonyl chloride.

Example 7

7,13-Bis((1-adamantyl)acetyl)-1,4,10-trioxa-7,13-diazacyclopentadecane

Analogously to Example 2 from 1,4,10-trioxa-7,13-diazacyclopentadecane and (1-adamantyl) acetyl chloride.

Example 8

4,13-Bis(tert.-butylcarbonyl)-1,7,10,16-tetraoxa-4,13-diazacyclooctadecane Analogously to Example 2 from 1,7,10,16-tetraoxa-4,13-diazacyclooctadecane and pivalyl chloride.

Example 9

4,13-Bis(1-adamantylcarbonyl)-1,7,10,16-tetraoxa-4,13-diazacyclooctadecane Analogously to Example 2 from 1,7,10,16-tetraoxa-4,13-diazacyclooctadecane and 1-adamantylcarbonyl chloride.

Example 10

4,13-Bis((1-adamantyl)acetyl)-1,7,10,16-tetraoxa-4,13-diazacyclooctadecane Analogously to Example 2 from 1,7,10,16-tetraoxa-4,13-diazacyclooctadecane (1adamantyl)acetyl chloride.

Example 11

4,16-Bis(tert.,-butylcarbonyl)-1,7,10,13,19-pentaoxa-4,16-diazacycloheneicosane Analogously to Example 2 from 1,7,10,13,19-pentaoxa-4,16-diazacycloheneicosane and pivalyl chloride.

Example 12

4,16-Bis(1-adamantylcarbonyl)-1,7,10,13,19-pentaoxa-4,16-diazacycloheneicosane Analogously to Example 2 from 0,13,19-pentaoxa-4,16-diazacycloheneicosane and 1-adamantylcarbonyl chloride.

Example 13

4,4
16-Bis((1-adamantyl)acetyl)-1,7,10,13,19-pentaoxa-4,16-diazacycloheneicosane Analogously to Example 2 from 1,7,10,13,19-pentaoxa-4,16-diazacycloheneicosane and (1-adamantyl)acetyl chloride.

Example 14

1-(Tert.-butylcarbonyl)-1-aza-4,7,10-trioxacyclododecane 3.81 mmol of 1-aza-4,7,10-trioxacyclododecane are dissolved in 50 ml of $CH_2Cl_2$. 0.6 ml of triethylamine are added and 0.1 g of DMAP (=4-dimethylaminopyridine) is added as catalyst 3.82 mmol of pivalyl chloride are subsequently added, and the mixture is stirred at room temperature for 18 hours.

The reaction solution is washed twice with 1N HCl and subsequently twice with saturated $NaHCO_3$ solution and dried over $MgSO_4$, and the solvent is stripped off. The crude product is purified by column chromatography on silica gel using $CH_2Cl_2$/methanol=20/1.

Example 15

1-(1-Adamantylcarbonyl)-1-aza-4,7,10-trioxacyclododecane

Analogously to Example 14 from 1-aza-4,7,10-trioxacyclododecane and 1-adamantylcarbonyl chloride.

Example 16

1-((1-Adamantyl)acetyl)-1-aza-4,7,10-trioxacyclododecane

Analogously to Example 14 from 1-aza-4,7,10-trioxacyclododecane and (1-adamantyl)acetyl chloride.

Example 17

1-(Tert.-butylcarbonyl)-1-aza-4,7,10,13-tetraoxacyclopentadecane

Analogously to Example 14 from 1-aza-4,7,10,13-tetraoxacyclopentadecane(13-1,4,7,10) and pivalyl chloride.

Example 18

1-(1-Adamantylcarbonyl)-1-aza-4,7,10,13-tetraoxacyclopentadecane

Analogously to Example 14 from 1-aza-4,7,10,13-tetraoxacyclopentadecane and 1-adamantylcarbonyl chloride.

Example 19

1-((1-Adamantyl)acetyl)-1-aza-4,7,10,13-tetraoxacyclopentadecane

Analogously to Example 14 from 1-aza-4,7,10,13-tetraoxacyclopentadecane and (1-adamantyl)acetyl chloride.

Example 20

1-(Tert.-butylcarbonyl)-1-aza-4,7,10,13,16-pentaoxacyclooctadecane

Analogously to Example 14 from 1-aza-4,7,10,13,16-pentaoxacyclooctadecane and pivalyl chloride.

Example 21

1-(1-Adamantylcarbonyl)-1-aza-4,7,10,13,16-pentaoxacyclooctadecane

Analogously to Example 14 from 1-aza-4,7,10,13,16-pentaoxacyclooctadecane and 1-adamantylcarbonyl chloride.

Example 22

1-((1-Adamantyl)acetyl)-1-aza-4,7,10,13,16-pentaoxacyclooctadecane

Analogously to Example 14 from 1-aza-4,7,10,13,16-pentaoxacyclooctadecane and (1-adamantyl) acetyl chloride.

Example 23

1-(Tert.-butylcarbonyl)-1-aza-4,7,10,13,16,19-hexaoxacycloheneicosane

Analogously to Example 14 from 1-aza-4,7,10,13,16,19-hexaoxacycloheneicosane and pivalyl chloride.

Example 24

1-(1-Adamantylcarbonyl)-1-aza-4,7,10,13,16,19-hexaoxacycloheneicosane

Analogously to Example 14 from 1-aza-7,10,13,16,19-hexaoxacycloheneicosane and 1-adamantylcarbonyl chloride.

Example 25

1-((1-Adamantyl)acetyl)-1-aza-4,7,10,13,16,19-hexaoxacycloheneicosane

Analogously to Example 14 from 1-aza-4,7,10,13,16,19-hexaoxacycloheneicosane and (1-adamantyl)acetyl chloride.

Example 26

4,10-Bis(2,2-dimethylbutyroyl)-1,7-dioxa-4,10-diazacyclododecane

Analogously to Example 2 from 1,7-dioxa-4,10-diazacyclododecane and 2,2-dimethylbutyryl chloride.

Example 27

7,13-Bis(2,2-dimethylbutyroyl)-1,4,10-trioxa-7,13-diazacyclopentadecane

Analogously to Example 2 from 1,4,10-trioxa-7,13-diazacyclopentadecane and 2,2-dimethylbutyryl chloride.

Example 28

4,13-Bis(2,2-dimethylbutyroyl)-1,7,10,16-tetraoxa-4,13-diazacyclooctadecane Analogously to Example 2 from 1,7,10,16-tetraoxa-4,13-diazacyclooctadecane and 2,2-dimethylbutyryl chloride.

Example 29

4,16-Bis(2,2-dimethylbutyroyl)-1,7,10,13,19-pentaoxa-4,16-diazacycloheneicosane Analogously to Example 2 from 1,7,10,13,19-pentaoxa-4,16-diazacycloheneicosane and 2,2-dimethylbutyryl chloride.

Example 30

1-(2,2-Dimethylbutyroyl)-1-aza-4,7,10-trioxacyclododecane

Analogously to Example 14 from 1-aza-4,7,10-trioxacyclododecane and 2,2-dimethylbutyryl chloride.

Example 31

1-(2,2-Dimethylbutyroyl)-1-aza-4,7,10,13-tetraoxacyclopentadecane

Analogously to Example 14 from 1-aza-4,7,10,13-tetraoxacyclopentadecane and 2,2-dimethylbutyryl chloride.

Example 32

1-(2,2-Dimethylbutyroyl)-1-aza-4,7,10,13,16-pentaoxacyclooctadecane

Analogously to Example 14 from 1-aza-4,7,10,13,16-pentaoxacyclooctadecane and 2,2-dimethylbutyryl chloride.

Example 33

1-(2,2-Dimethylbutyroyl)-1-aza-4,7,10,13,16,19-hexaoxacycloheneicosane

Analogously to Example 14 from 1-aza-4,7,10,13,16,19-hexaoxacycloheneicosane and 2,2-dimethylbutyryl chloride.

Example 34

4,10-Bis(3,3-dimethylbutyroyl)-1,7-dioxa-4,10-diazacyclododecane

Analogously to Example 2 from 1,7-dioxa-4,10-diazacyclododecane and 3,3-dimethylbutyryl chloride.

Example 35

7,13-Bis(3,3-dimethylbutyroyl)-1,4,10-trioxa-7,13-diazacyclopentadecane

Analogously to Example 2 from 1,4,10-trioxa-7,13-diazacyclopentadecane and 3,3-dimethylbutyryl chloride.

Example 36

4,13-Bis(3,3-dimethylbutyroyl)-1,7,10,16-tetraoxa-4,13-diazacyclooctadecane Analogously to Example 2 from 1,7,10,16-tetraoxa-4,13-diazacyclooctadecane and 3,3-dimethylbutyryl chloride.

Example 37

4,16-Bis(3,3-dimethylbutyroyl)-1,7,10,13,19-pentaoxa-4,16-diazacycloheneicosane Analogously to Example 2 from 1,7,10,13,19-pentaoxa-4,16-diazacycloheneicosane and 3,3-dimethylbutyryl chloride.

Example 38

1-(3,3-Dimethylbutyroyl)-1-aza-4,7,10-trioxacyclododecane

Analogously to Example 14 from 1-aza-4,7,10-trioxacyclododecane and 3,3-dimethylbutyryl chloride.

Example 39

1-(3,3-Dimethylbutyroyl)-1-aza-4,7,10,13-tetraoxacyclopentadecane

Analogously to Example 14 from 1-aza-4,7,10,13-tetraoxacyclopentadecane and 3,3-dimethylbutyryl chloride.

Example 40

1-(3,3-Dimethylbutyroyl)-1-aza-4,7,10,13,16-pentaoxacyclooctadecane

Analogously to Example 14 from 1-aza-4,7,10,13,16-pentaoxacyclooctadecane and 3,3-dimethylbutyryl chloride.

Example 41

1-(3,3-Dimethylbutyroyl)-1-aza-4,7,10,13,16,19-hexaoxacycloheneicosane

Analogously to Example 14 from 1-aza-4,7,10,13,16,19-hexaoxacycloheneicosane and 3,3-dimethylbutyryl chloride.

Example 42

4,10-Bis(1-noradamantylcarbonyl)-1,7-dioxa-4,10-diazacyclododecane

Analogously to Example 2 from 1,7-dioxa-4,10-diazacyclododecane and 1-noradamantanecarbonyl chloride.

Example 43

7,13-Bis(1-noradamantylcarbonyl)-1,4,10-trioxa-7,13-diazacyclopentadecane Analogously to Example 2 from 1,4,10-trioxa-7,13-diazacyclopentadecane and 1-noradamantanecarbonyl chloride.

Example 44

4,13-Bis(1-noradamantylcarbonyl)-1,7,10,16-tetraoxa-4,13-diazacyclooctadecane Analogously to Example 2 from 1,7,10,16-tetraoxa-4,13-diazacyclooctadecane and 1-noradamantanecarbonyl chloride.

Example 45

4,16-Bis(1-noradamantylcarbonyl)-1,7,10,13,19-pentaoxa-4,16-diazacycloheneicosane Analogously to Example 2 from 1,7,10,13,19-pentaoxa-4,16-diazacycloheneicosane and 1-noradamantanecarbonyl chloride.

Example 46

1-(1-Noradamantylcarbonyl)-1-aza-4,7,10-trioxacyclododecane

Analogously to Example 14 from 1-aza-4,7,10-trioxacyclododecane and 1-noradamantanecarbonyl chloride.

Example 47

1-(1-Noradamantylcarbonyl)-1-aza-4,7,10,13-tetraoxacyclopentadecane

Analogously to Example 14 from 1-aza-4, 7, 10, 13-tetraoxacyclopentadecane and 1-noradamantanecarbonyl chloride.

Example 48

1-(1-Noradamantylcarbonyl)-1-aza-4,7,10,13,16-pentaoxacyclooctadecane

Analogously to Example 14 from 1-aza-4,7,10,13,16-pentaoxacyclooctadecane and 1-noradamantanecarbonyl chloride.

Example 49

1-(1-Noradamantylcarbonyl)-1-aza-4,7,10,13,16,19-hexaoxacycloheneicosane

Analogously to Example 14 from 1-aza-4,7,10,13,16,19-hexaoxacycloheneicosane and 1-noradamantanecarbonyl chloride. Example 50

Use example—verification of stability

In order to verify the increased chemical stability of the compounds according to the invention, Z1 and Kryptofix 22, which is known to be photosensitive, are added to a liquid-crystalline mixture.

The two samples were irradiated for 30 minutes at 50° C. using a UV lamp (Sun Tester from Heraeus). The irradiated samples were subsequently dissolved in methylene chloride, and the corresponding optical spectra recorded using a photometer. The reference used was a pure liquid crystal dissolved in methylene chloride.

Z1:

Kryptofix 22

Figure 1:
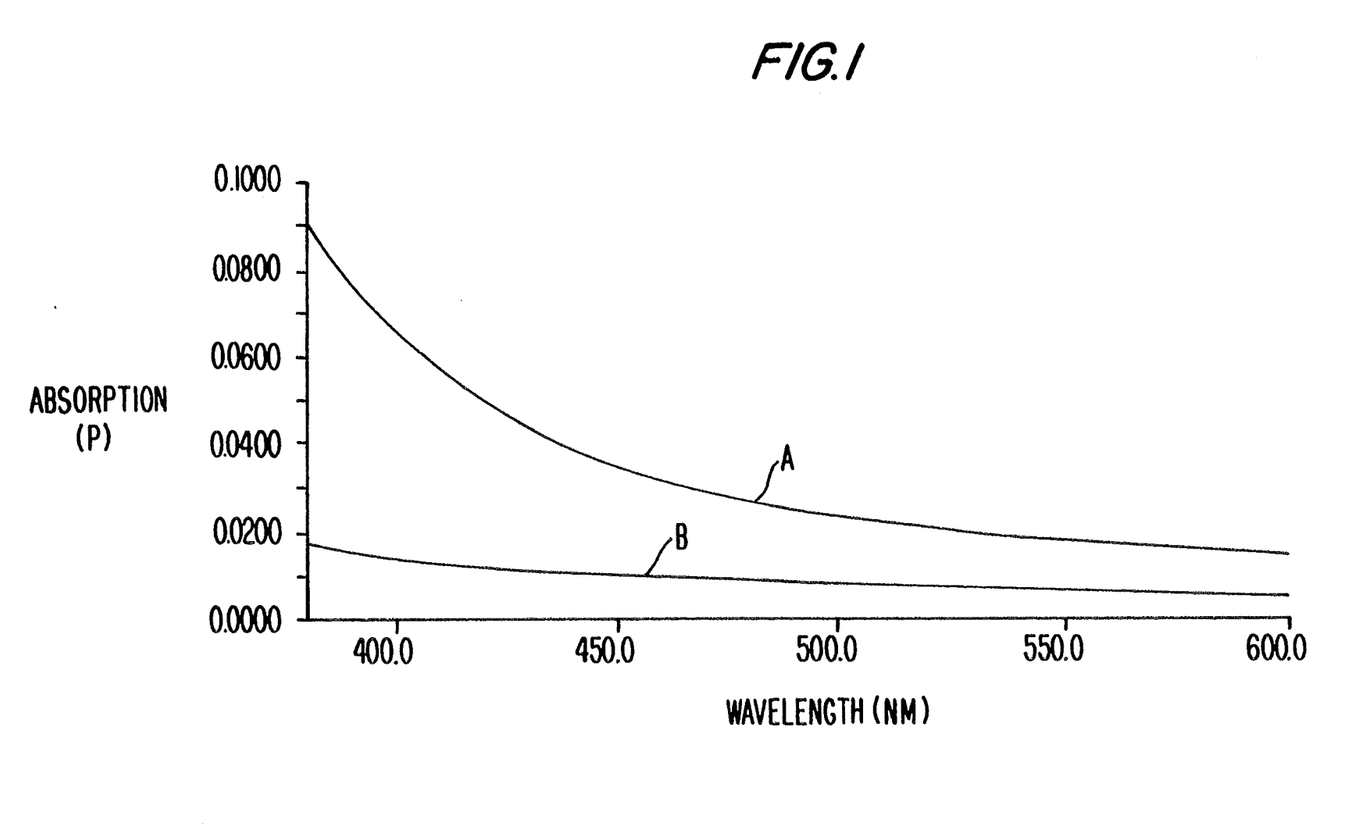
FIG. 1 shows the optical spectra of the liquid crystal mixture containing Kryptofix 22 (curve A) and of the mixture containing Z1 (curve B).

The figure shows the optical spectra of the liquid-crystal mixture containing Kryptofix 22 (curve A) and of the mixture containing Z1 (curve B), The yellow coloration of the sample produced on decomposition of Kryptofix 22 results in an absorption in the spectrum in a range between 400 and 500 nm. The mixture containing the compounds according to the invention exhibits no significant absorption in this range.

We claim:

1. A compound of the formula I in which

$Z^1$, $Z^2$, $Z^3$, $Z^4$, $Z^5$ and $Z^6$ are identical or different and are the —O—, groups, or are a single bond, but where at least 3 of the Z groups must be present in the formula I,
and where $R^1$ and $R^2$ are identical or different and are $C_1$-$C_{18}$alkyl or phenyl, which may be substituted by 1 to 3 $C_1$-$C_4$—alkyl or -alkoxy groups, or $R^1$ and $R^2$ together are —$(CH_2)_5$— or —$(CH_2)_6$—, and $R^3$ is hydrogen or $C_1$-$C_4$-alkyl, Y is the B—$(CH_2)_m$—A— group, in which A is B is the group, where $R^9$, $R^{10}$ and $R^{11}$ are identical or different and are branched or unbranched alkyl having 1 to 6 carbon atoms, or together with the carrying carbon atom form a cyclic or polycyclic system having 2 to 12 rings, m is the number 0 or 1,

X is N-Y, —O— or $Z^1$ to $Z^{6,}$ a, b, c, d, e, f, g, h, i, j, k and l are a number from 0 to 3, where the sum of a+b+c+d+e+f+g+h+i+j+k+ corresponds to from 8 to 16 carbon atoms, with the proviso that if a, f, g and/or l are the number zero only the groups are bonded directly to N or X, and that $Z^1$, $Z^2$ and $Z^3$, and $Z^4$, $Z^5$ and $Z^6$ are not directly adjacent, and p, q, r, s, t and u are the number 0 or 1, where the sum of p, q, r, s, t and u is from 3 to a, b, c, d, e, f, g, h, i, j, k, l and p, q, r, s, t and u must be selected so that ring sizes of from 12 to 24, arise.

2. A compound as claimed in claim 1, namely 1-(Tert-butylcarbonyl)-1-aza-4,7,10,13-tetraoxacyclopentadecane

3. A compound as claimed in claim 1, namely 1-(1-Adamantylcarbonyl)-1-aza-4,7,10,13-tetraoxacyclopentadecane 4. A compound as claimed in claim 1, namely 1-(Tert-butylcarbonyl)-1-aza-4,7,10,13,16-pentaoxacyclooctadecane 5. A compound as claimed in claim 1, namely 1-(1-Adamantylcarbonyl)-1-aza-4,7,10,13,16-pentaoxacyclooctadecane 6. A process for the light- and heat-stabilization of nitrogen-containing complex ligands in ferroelectric liquid-crystal mixtures or alignment layers, which comprises derivatizing the complex ligands at the nitrogen by means of bulky secondary or tertiary carboxylic acids or sulfonic acids to give compounds of the formula (I) in claim 1.

7. A liquid-crystal mixture which contains from 0.01 to 20% by weight of at least one compound of the formula I as claimed in claim 1.

8. An alignment layer which contains from 0.01 to 20% by weight of at least one compound of the formula I as claimed in claim 1.

9. An electro-optical switching and display element containing a liquid-crystal mixture or an alignment layer on both as claimed in claim 7 or 8.

10. A liquid-crystal mixture as claimed in claim 7 which is ferroelectric.

* * * * *